(12) United States Patent
Long et al.

(10) Patent No.: US 11,452,809 B2
(45) Date of Patent: Sep. 27, 2022

(54) APPARATUSES, SYSTEMS, AND METHODS FOR THE TREATMENT OF A TISSUE SITE WITH NEGATIVE PRESSURE AND OXYGEN

(71) Applicant: KCI Licensing, Inc., San Antonio, TX (US)

(72) Inventors: Justin Alexander Long, Lago Vista, TX (US); Christopher Brian Locke, Bournemouth (GB); Timothy Mark Robinson, Shillingstone (GB); Richard Daniel John Coulthard, Verwood (GB)

(73) Assignee: KCI Licensing, Inc., San Antonio, TX (US)

( * ) Notice: Subject to any disclaimer, the term of this patent is extended or adjusted under 35 U.S.C. 154(b) by 112 days.

(21) Appl. No.: 16/495,952

(22) PCT Filed: Feb. 21, 2018

(86) PCT No.: PCT/US2018/019031
§ 371 (c)(1),
(2) Date: Sep. 20, 2019

(87) PCT Pub. No.: WO2018/186941
PCT Pub. Date: Oct. 11, 2018

(65) Prior Publication Data
US 2020/0023105 A1    Jan. 23, 2020

Related U.S. Application Data

(60) Provisional application No. 62/481,549, filed on Apr. 4, 2017.

(51) Int. Cl.
*A61M 1/00*   (2006.01)
*A61F 13/00*  (2006.01)

(52) U.S. Cl.
CPC ......... *A61M 1/85* (2021.05); *A61F 13/00068* (2013.01); *A61M 1/90* (2021.05);
(Continued)

(58) Field of Classification Search
CPC .............. A61M 1/0084; A61M 1/0088; A61M 2202/0208; A61M 2205/3344; A61M 1/85; A61M 1/90; A61F 13/00068
See application file for complete search history.

(56) References Cited

U.S. PATENT DOCUMENTS 1,355,846 A    10/1920   Rannells
2,547,758 A    4/1951    Keeling
(Continued)

FOREIGN PATENT DOCUMENTS

AU    550575 B2    3/1986
AU    745271 B2    3/2002
(Continued)

OTHER PUBLICATIONS

"What is an Electronic Controller?", Trerice, Jan. 1, 2001, http://www.cpinc.com/trerice/Control/control_43_44.pdf (Year: 2001).*
(Continued)

*Primary Examiner* — Ariana Zimbouski

(57) ABSTRACT

In an example is a system for providing treatment to a tissue site. The system may include a tissue interface for transporting fluid to the tissue site. The system may further include a cover for providing a sealed space including the tissue interface. The system may further include a negative-pressure source fluidly coupled to the tissue interface and providing negative pressure. The system may further include a hyperoxic fluid source fluidly coupled to the tissue interface and providing a hyperoxic fluid. The system may further include a controller for controlling the negative pressure and the hyperoxic fluid so as to maintain the sealed
(Continued)

space at a negative pressure while the hyperoxic fluid is provided to the sealed space.

18 Claims, 6 Drawing Sheets

(52) U.S. Cl.
CPC ............... *A61M 2202/0208* (2013.01); *A61M 2205/3344* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2010/0160853 A1* | 6/2010 | Smith | A61F 13/00063 604/23 |
| 2011/0034861 A1* | 2/2011 | Schaefer | A61M 35/30 604/23 |
| 2011/0130712 A1* | 6/2011 | Topaz | A61F 13/00068 604/23 |
| 2013/0303975 A1* | 11/2013 | Gvodas, Jr. | A61M 35/30 604/23 |
| 2014/0163491 A1 | 6/2014 | Schuessler et al. | |
| 2014/0316330 A1 | 10/2014 | Fudem et al. | |
| 2014/0336564 A1* | 11/2014 | Felding | A61F 13/00068 604/23 |
| 2015/0080788 A1 | 3/2015 | Blott et al. | |
| 2015/0290364 A1* | 10/2015 | Wall | A61M 1/90 604/23 |
| 2016/0166781 A1* | 6/2016 | Sarangapani | A61M 1/0023 604/23 |
| 2016/0175500 A1 | 6/2016 | Cali et al. | |
| 2016/0325028 A1* | 11/2016 | Locke | A61F 13/00068 |
| 2017/0049627 A1* | 2/2017 | Sexton | A61M 1/0088 |

(56) References Cited

U.S. PATENT DOCUMENTS

| | | | |
|---|---|---|---|
| 2018/0050137 A1* | 2/2018 | Ryu | A61M 1/74 |
| 2020/0121510 A1* | 4/2020 | Hartwell | A61F 13/00068 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 0007653 A1 | 2/2000 |
| WO | 2009141820 A1 | 11/2009 |
| WO | 2011017542 A1 | 2/2011 |

OTHER PUBLICATIONS

International Search Report and Written Opinion for corresponding Application No. PCT/US2018/019031, dated May 25, 2018.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sept. 3, 1997.
Dattilo, Philip P., Jr., et al; "Medical Textiles: Application of an Absorbable Barbed Bi-directional Surgical Suture" Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and ceilified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

(56) References Cited

OTHER PUBLICATIONS

C.E. Tennants, The Use of Hypermia in the Postoperative Treatment of Lesions of the Extremities and Thorax, Journal of the American Medical Association 64 (1915), pp. 1548-1549.
Selections from W. Meyer and V. Schmieden, Bier's Hyperemic Treatment in Surgery, Medicine, and the Specialties: A Manual of its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

\* cited by examiner

APPARATUSES, SYSTEMS, AND METHODS FOR THE TREATMENT OF A TISSUE SITE WITH NEGATIVE PRESSURE AND OXYGEN

RELATED APPLICATIONS

The present invention claims the benefit, under 35 USC § 119(e), of the filing of U.S. Provisional Patent Application Ser. No. 62/481,549, entitled "Apparatuses, Systems, And Methods For The Treatment Of A Tissue Site With Negative Pressure And Oxygen," filed Apr. 4, 2017. This provisional application is incorporated herein by reference for all purposes.

TECHNICAL FIELD

The subject matter disclosed herein and recited in the appended claims relates generally to tissue treatment systems and more particularly, but without limitation, to apparatuses, systems, and methods for the treatment of a tissue site with negative pressure and oxygen.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating tissue sites, particularly, wounds. Regardless of the etiology of a wound, whether trauma, surgery, or another cause, proper care of the wound is important to the outcome. Treatment of wounds or other tissue sites with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can also be beneficial for new tissue growth. For example, a liquid solution can be used to wash out a wound or, likewise, a cavity, for example, for therapeutic purposes. These practices are commonly referred to as "irrigation" and "lavage" respectively. "Instillation" is another practice that generally refers to a process of introducing a fluid to a tissue site and leaving the fluid in contact with the tissue site for a prescribed period of time before removing the fluid.

While the clinical benefits of negative-pressure therapy and instillation therapy are widely known, improvements to therapy systems, components, and processes may benefit healthcare providers and patients.

BRIEF SUMMARY

New and useful systems, apparatuses, and methods for a therapy including the provision of negative pressure and oxygen are set forth in the appended claims. Illustrative embodiments are also provided to enable a person skilled in the art to make and use the claimed subject matter.

For example, in some embodiments disclosed herein is a system for providing treatment to a tissue site. The system may comprise a tissue interface configured to transport fluid to the tissue site. The system may further comprise a cover configured to provide a sealed space that includes the tissue interface. The system may still further comprise a negative-pressure source fluidly coupled to the tissue interface and configured to provide negative pressure. The system may still further comprise a hyperoxic fluid source fluidly coupled to the tissue interface and configured to provide a hyperoxic fluid. The system may still further comprise a controller. The controller may be configured to control the negative pressure and the hyperoxic fluid so as to maintain the sealed space at a negative pressure while the hyperoxic fluid is provided to the sealed space.

Also disclosed herein in some embodiments is a method of providing treatment to a tissue site. The method may comprise applying a tissue interface to the tissue site. The method may further comprise providing a sealed space around the tissue interface. The method may still further comprise reducing pressure of the sealed space. The method may still further comprise delivering a hyperoxic fluid to the sealed space while maintaining the sealed space at a negative pressure.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Negative Pressure and Oxygen Therapy System

Figure 1:
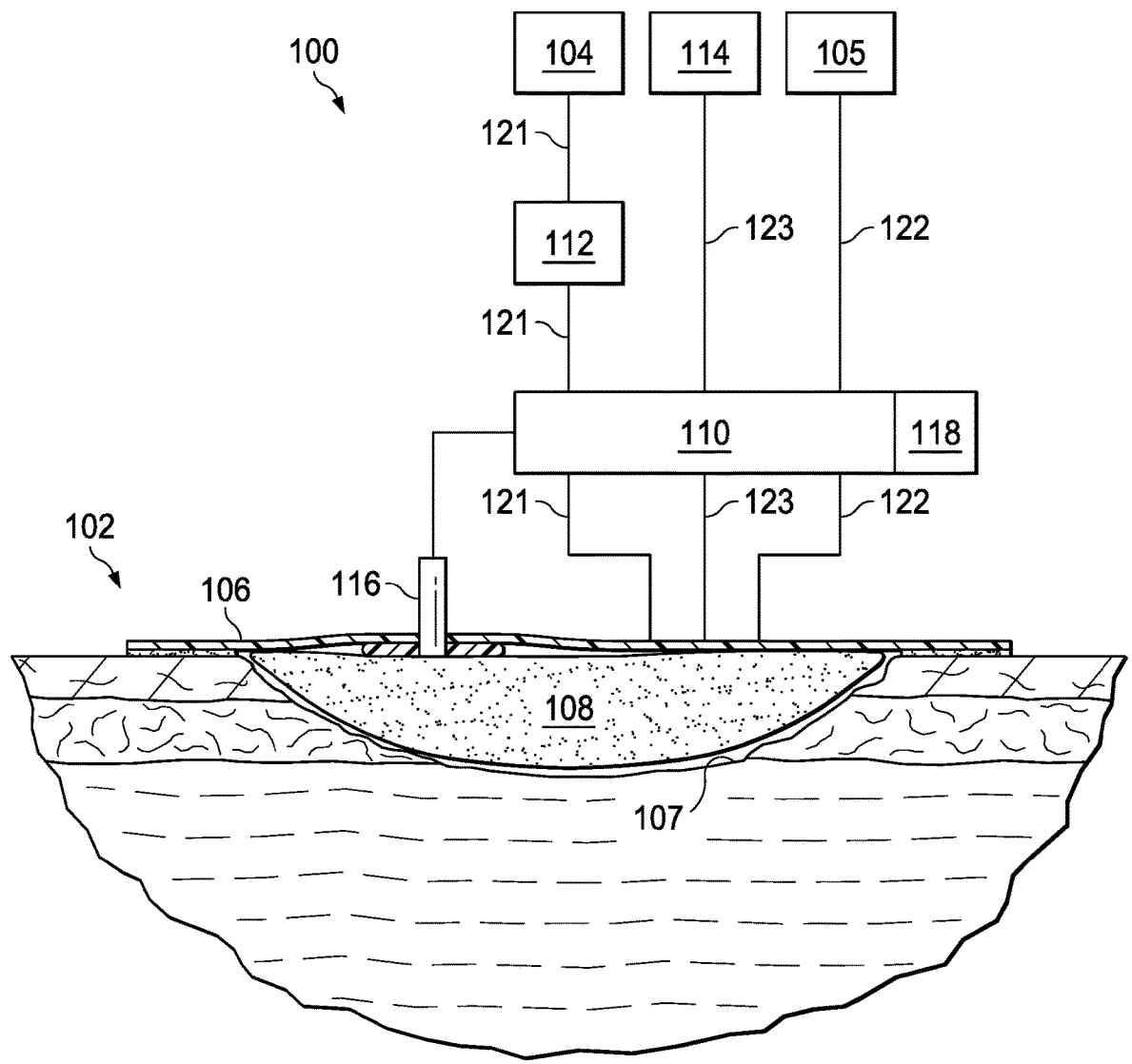
FIG. 1 is a functional schematic of an embodiment of a therapy system for use in negative pressure and oxygen therapy in accordance with this specification.

Disclosed herein are embodiments of apparatuses, systems, and methods for the treatment of a tissue site with negative pressure and oxygen, which may be referred to herein as "negative pressure and oxygen" therapy. Referring to FIG. 1, an embodiment of a therapy system 100 for use in negative pressure and oxygen therapy is shown in a simplified functional schematic. Generally, and as will be disclosed herein, the therapy system 100 may be configured to provide negative-pressure and oxygen to a tissue site.

As used herein the term "tissue site" is intended to broadly refer to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include a chronic, acute, traumatic, subacute, and dehisced wound, a partial-thickness burn, an ulcer (such as diabetic, pressure, or venous insufficiency ulcers), a flap, or a graft, for example. Also, the term "tissue site" may also refer to areas of any tissue that are not necessarily wounded or defective, but are instead areas in which it may be desirable to add or promote the growth of additional tissue.

In various embodiments, a therapy system may generally include a negative-pressure supply and a hyperoxic fluid source, which may directly or indirectly be coupled to or may be configured to be coupled to a distribution component. In general, a distribution component, such as a wound dressing, may refer to any complementary or ancillary component configured to be fluidly coupled to a negative-pressure supply and/or hyperoxic fluid source, for example, within or forming a part of a fluid path between one or both of the negative-pressure supply and the hyperoxic fluid source and a tissue site. A distribution component may be detachable, and may be disposable, reusable, or recyclable. Also, in some embodiments, the therapy system may include a source of instillation fluids, which may also be directly or indirectly coupled to the distribution component. In some embodiments, a therapy system like the therapy system 100 of FIG. 1 may comprise a regulator or a controller.

For example, in the embodiment of FIG. 1, the therapy system 100 may generally include a negative-pressure source 104, a hyperoxic fluid source 105, and a solution source 114, each fluidly coupled to a dressing 102. The therapy system 100 also includes a therapy system controller 110 generally configured to control the application of negative pressure and the application of hyperoxic fluid to the dressing 102.

Negative-Pressure Source

As used herein, "negative pressure" is generally intended to refer to a pressure less than a local ambient pressure, such as the ambient pressure in a local environment external to a sealed therapeutic environment provided by the dressing 102. In many cases, the local ambient pressure may also be the atmospheric pressure proximate to or about a tissue site. Alternatively, the pressure may be less than a hydrostatic pressure associated with the tissue at the tissue site. Unless otherwise indicated, values of pressure stated herein are gauge pressures. Similarly, references to increases in negative pressure typically refer to a decrease in absolute pressure, for example, a "more negative" pressure, while decreases in negative pressure typically refer to an increase in absolute pressure, for example, a "less negative" pressure or a "more positive" pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The fluid mechanics associated with the use of a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," "communicating," or "generating" negative pressure, for example.

In general, fluid, such as exudates and other fluids, flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

In various embodiments, a negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. A negative-pressure supply may also have one or more supply ports configured to facilitate coupling and de-coupling of the negative-pressure supply to one or more distribution components. Additionally, in some embodiments, the therapy system 100 may include a fluid container. For example, in the embodiment of FIG. 1, the therapy system 100 includes a container 112 fluidly coupled to the dressing 102 and to the negative-pressure source 104. The container 112 is representative of a canister, pouch, or other container or storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

In various embodiments, two or more of the various components of the therapy system 100 may be fluidly coupled to each other to provide a path for transferring fluids, such as liquids and/or gases, between the components. For example, components may be fluidly coupled through a fluid conductor, such as a tube. As used herein, the term "tube" may broadly include a tube, pipe, hose, conduit, or other structure with one or more lumina adapted to convey a fluid between two ends thereof. Typically, a tube is an elongated, cylindrical structure with some flexibility, but the geometry and rigidity may vary. In some embodiments, two or more components may also be coupled by virtue of physical proximity, being integral to a single structure, or being formed from the same piece of material. Moreover, some fluid conductors may be molded into or otherwise integrally combined with other components. Additionally, coupling may also include mechanical, thermal, electrical, or chemical coupling (such as a chemical bond) in some contexts. For example, a tube may mechanically and fluidly couple the dressing 102 to the container 112 in some embodiments. In general, components of the therapy system 100 may be coupled directly or indirectly.

For example, in the embodiment of FIG. 1, the negative-pressure source 104 is configured to provide negative pressure to the dressing 102. For example, the negative-pressure source 104 may be indirectly coupled to the dressing 102, for example, through the container 112.

In some embodiments, the negative-pressure source 104 may comprise a controller, for example, a negative pressure-source controller. In such an embodiment, the negative-pressure source controller may generally be configured to control the operation of the negative-pressure source 104 according to one or more inputs.

Hyperoxic Fluid Source

"Hyperoxic fluid" may generally refer to a fluid having oxygen at greater than atmospheric concentrations (which may generally be about 20.95% $O_2$), for example, a fluid where the oxygen exhibits a partial pressure greater than the partial pressure of oxygen in air at about sea level (which may generally be about 159 mmHg). Unless otherwise apparent from the context, the term "oxygen," may refer to elemental oxygen ($O_2$), for example, "diatomic oxygen," "dioxygen," or "oxygen gas." For example, in various embodiments, the hyperoxic fluid may be liquidus or gaseous, for example, a liquid having dissolved $O_2$. In various embodiments, the hyperoxic fluid may comprise at least about 50% $O_2$ by weight, or more specifically, at least about 60% $O_2$ by weight, or more specifically, at least about 70% $O_2$ by weight, or more specifically, at least about 80% $O_2$ by weight, or more specifically, at least about 90% $O_2$ by weight, or more specifically, at least about 95% $O_2$ by weight, or more specifically, at least about 99% $O_2$ by weight of the fluid.

In various embodiments, the hyperoxic fluid source 105, may be a reservoir of a hyperoxic fluid or a device that, when operated, can generate a volume of a hyperoxic fluid. In some embodiments, for example, the hyperoxic fluid source 105 may comprise both an oxygen generator and a reservoir of hyperoxic fluid. In some embodiments, the hyperoxic fluid source 105 may be configured to generate the hyperoxic fluid by one or more chemical reactions, such as by chemical oxygen generation. For example, in some embodiments, the hyperoxic fluid source 105 is configured to operate based upon a hydrolysis technique, for example, where oxygen is yielded from a hydrolytic reaction from water vapor taken from the air.

Additionally or alternatively, in some embodiments, the hyperoxic fluid source 105 may be configured to concentrate oxygen within a fluid, for example, an oxygen concentrator. For example, the hyperoxic fluid source 105 may be an oxygen concentrator configured to operate based upon the principle of pressure swing adsorption (PSA), which adsorbs gases onto a molecular sieve. More particularly, atmospheric nitrogen may be preferentially adsorbed onto a zeolite mineral(s), for example, by rapid pressure swing adsorption, and then the previously adsorbed nitrogen may be vented, for example, leaving behind concentrated oxygen. Examples of suitable, commercially-available oxygen concentrators include an Oxysure™ device available from Oxysure Therapeutics, and the Airsep Focus Portable Oxygen Concentrator, available from Caire Medical.

The hyperoxic fluid source 105 may also have one or more supply ports configured to facilitate coupling and de-coupling of the hyperoxic fluid source 105 to one or more distribution components. The hyperoxic fluid source 105 may be configured to provide a hyperoxic fluid to a wound dressing. In the embodiment of FIG. 1, the hyperoxic fluid source 105 is in fluid communication with the dressing 102.

In some embodiments, the hyperoxic fluid source 105 may comprise a controller, for example, a hyperoxic fluid source controller. In such an embodiment, the hyperoxic fluid source controller may generally be configured to control the operation of the hyperoxic fluid source according to one or more inputs.

Instillation Solution

In some embodiments, the therapy system 100 may also include a source of instillation solution, for example, an instillation fluid. For example, referring again to the embodiment of FIG. 1, the therapy system 100 includes the solution source 114. In various embodiments, the solution source 114 may also comprise a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In some embodiments, the solution source 114 may comprise a manual or electrically-powered device configured to deliver a volume of the instillation solution, for example, a pump, such as a positive-displacement pump or metering pump. Also, in some embodiments, the solution source 114 may comprise a controller, for example, a solution source controller. In such an embodiment, the solution source controller may generally be configured to control the operation of the solution source 114 according to one or more inputs.

Wound Dressing

In various embodiments, the dressing 102 may include a cover and one or more tissue interface layers, for example, primary and secondary layer interface layers. For example, in the embodiment of FIG. 1, the dressing 102 includes a cover 106 and an interface layer 108.

In various embodiments, the cover 106 may generally be configured to provide a barrier between a sealed space 107, for example, a sealed therapeutic environment, and the local external environment. The cover 106 may form, for example, a bacterial barrier and/or protection from physical trauma. For example, the cover 106 may also be constructed from a material that can reduce evaporative losses and provide a fluid seal between the sealed space 107 and the local external environment. The cover 106 may be, for example, an elastomeric film or membrane that can provide a seal adequate to maintain a negative pressure at a tissue site for a given negative-pressure source. In some embodiments, the cover 106 may have a high moisture-vapor transmission rate (MVTR), for example, for some applications. In such an embodiment, the MVTR may be at least 300 g/m$^2$ per twenty-four hours. In some embodiments, the cover 106 may be formed from a suitable polymer. For example, the cover 106 may comprise a polymer drape, such as a polyurethane film, that is permeable to water vapor but generally impermeable to liquid. In such embodiments, such drapes have a thickness in the range of about 25 to about 50 microns. In embodiments where the cover comprises a permeable material, the cover 106 may have a permeability sufficiently low that a desired negative pressure may be maintained.

In some embodiments, the cover 106 may be configured to be attached to an attachment surface, such as undamaged epidermis, a gasket, or another cover, for example, via an attachment device. In such embodiments, the attachment device may take any suitable form. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g. s. m.). Thicker adhesives, or combinations of adhesives, may be applied in some embodiments, for example, to improve the seal and reduce leaks. Other example embodiments of an attachment device may include a double-sided tape, a paste, a hydrocolloid, a hydrogel, a silicone gel, or an organogel.

In some embodiments, the cover 106 may be configured to facilitate fluid coupling of the negative-pressure source 104 and the hyperoxic fluid source 105 to the dressing 102. Additionally, in some embodiments, the cover may also be configured to facilitate fluid coupling of the solution source 114 to the dressing 102. For example, the cover 106 may include a first, second, and third port, such that the dressing may be fluidly coupled to the negative-pressure source 104, the hyperoxic fluid source 105, and the solution source 114, respectively.

In various embodiments, the interface layer 108 may be generally configured to distribute negative pressure, for example, so as to collect fluid from the tissue site. The interface layer 108 may also be configured to distribute hyperoxic fluid and/or to distribute the instillation fluid. For example, in some embodiments, the interface layer 108 may comprise or be configured as a manifold. A "manifold" in this context generally includes any composition or structure providing a plurality of pathways configured to collect or distribute fluid across a tissue site.

In various embodiments, the interface layer 108 may include a plurality of sublayers or, alternatively, only a single layer. Additionally, in some embodiments the interface layer 108 and/or various sublayers thereof may be configured for connection to the negative-pressure source 104, the hyperoxic fluid source 105, the solution source 114, or combinations thereof. For example, in the embodiment of FIG. 1, the interface layer 108 may be configured to receive negative pressure from the negative-pressure source 104 and to distribute negative pressure through the sealed space 107, which may have the effect of collecting fluid from the interface layer 108. Also in the embodiment of FIG. 1, the interface layer 108 may also be configured to receive hyperoxic fluid from the hyperoxic fluid source 105 and to distribute the hyperoxic fluid through the sealed space 107 and, also, to receive instillation fluid from the solution source and to distribute instillation fluid through the interface layer 108.

In various embodiments, the interface layer 108 or one or more sublayers forming the interface layer may comprise a fluid filter generally configured allow the application of negative pressure, instillation fluids, and/or hyperoxic fluids to tissue site while preventing or inhibiting the egress of fluids present at the tissue site, for example, within the sealed space 107. An example of a suitable fluid filter is the MMT 314 commercially available from W. M. Gore.

In some illustrative embodiments, the fluid pathways of a manifold may be interconnected to improve distribution or collection of fluids. For example, in some embodiments, a manifold may be a porous foam material having a plurality of interconnected cells or pores. For example, cellular foam, open-cell foam, reticulated foam, porous tissue collections, and other porous material such as gauze or felted mat generally include pores, edges, and/or walls adapted to form interconnected fluid pathways or channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

For example, in the embodiment of FIG. 1, the interface layer 108 comprises or is formed from a foam, such as an open-cell foam or a reticulated foam. In such an embodiment, the average pore size of such a foam may vary according to needs of a prescribed therapy. For example, in some embodiments, the interface layer 108 may be a foam having pore sizes in a range of 400-600 microns. The tensile strength of the interface layer 108 may also vary according to needs of a prescribed therapy. In one non-limiting example, the interface layer 108 may be an open-cell, reticulated polyurethane foam such as GRANUFOAM™ dressing or V. A. C. VERAFLO dressing, both available from Kinetic Concepts, Inc. of San Antonio, Tex.

The interface layer 108 may be either hydrophobic or hydrophilic. In an example in which the interface layer 108 may be hydrophilic, the interface layer 108 may also wick fluid away from the tissue site, for example, while also continuing to distribute negative pressure and hyperoxic fluid to the tissue site. In such an embodiment, the wicking properties of the interface layer 108 may draw fluid away from the tissue site by capillary flow or other wicking mechanisms. An example of a hydrophilic foam is a polyvinyl alcohol, open-cell foam such as V. A. C. WHITEFOAM™ dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

In some embodiments, the interface layer 108 may be constructed from bioresorbable materials. Suitable bioresorbable materials may include, but are not limited to, a polymeric blend of polylactic acid (PLA) and polyglycolic acid (PGA). The polymeric blend may also include without limitation polycarbonates, polyfumarates, and caprolactones. The interface layer 108 may further serve as a scaffold for new cell-growth, or a scaffold material may be used in conjunction with the interface layer 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In various embodiments, the interface layer 108 may also be generally configured to be in contact with the tissue site. For example, the interface layer 108 may be in contact with a portion of the tissue site, substantially all of the tissue site, or the tissue site in its entirety. If the tissue site is a wound, for example, the interface layer 108 may partially or completely fill the wound, or may be placed over or superior to the wound. In various embodiments, the interface layer 108 may take many forms, and may have many sizes, shapes, or thicknesses depending on a variety of factors, such as the type of treatment being implemented or the nature and size of a tissue site. For example, the size and shape of the interface layer 108 may be adapted to the contours of deep and irregular shaped tissue sites and/or may be configured so as to be adaptable to a given shape or contour. Moreover, in some embodiments, some or all of the surfaces of the interface layer 108 may comprise projections or an uneven, course, or jagged profile that can, for example, induce strains and stresses on a tissue site, for example, which may be effective to promote granulation at the tissue site.

Therapy System Controller

Generally, the therapy system controller 110 may be configured to control negative pressure, for example, from the negative-pressure source 104, and hyperoxic fluid, for example, from the hyperoxic fluid source 105, so as to maintain the sealed space 107 at a prescribed negative pressure while the hyperoxic fluid is also provided to the sealed space 107.

For example, in the embodiment of FIG. 1, the therapy system controller 110 may be configured to control the application of negative pressure to the sealed space 107 by controlling a route of fluid communication between the negative-pressure source 104 and the dressing 102, such as a first route of fluid communication 121. Likewise, the therapy system controller 110 may be configured to control the application of the hyperoxic fluid to the sealed space 107 by controlling a route of fluid communication between the hyperoxic fluid source 105 and the dressing 102, for example, a second route of fluid communication 122. Also, the therapy system controller 110 may be configured to control the application of instillation fluid to the sealed space 107 by controlling a route of fluid communication between the solution source 114 and the dressing 102, for example, a third route of fluid communication 123.

For example, in some embodiments, the therapy system controller 110 may generally be configured to control one or more parameters associated with the first route of fluid communication 121, the second route of fluid communication 122, or the third route of fluid communication 123, such that therapy system 100 is caused to maintain the sealed space 107 at a negative pressure while the hyperoxic fluid is provided to the sealed space 107. More particularly, the therapy system controller 110 may be configured to control one or more parameters associated with the first route of fluid communication 121, the second route of fluid communication 122, or the third route of fluid communication 123, such that therapy system 100 is caused to provide a desired negative pressure and oxygen, negative pressure, and oxygen therapy. Examples of such operating parameters may include the presence of absence of fluid-flow by way of various, particular routes of fluid communication and rate of fluid-flow and the rate of fluid-flow by way of the various, particular route of fluid communication.

In some embodiments, the therapy system controller 110 may comprise a microprocessor or other computing device or system (for example, a programmable logic controller or a data processing system). For instance, in some embodiments, the therapy system controller 110 may be a data processing system. A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code in order to reduce the number of times code is retrieved from bulk storage during execution.

In some embodiments, the therapy system controller 110 may be a programmable logic controller (PLC). A PLC may be a digital computer configured to receive one or more inputs and send one or more outputs in response to the one or more inputs. A PLC may include a non-volatile memory configured to store programs or operational instructions. In some embodiments, the non-volatile memory may be operationally coupled to a battery-back up so that the non-volatile memory retains the programs or operational instructions if the PLC otherwise loses power. In some embodiments, a PLC may be configured to receive discrete signals and continuous signals and produce discrete and continuous signals in response.

In various embodiments, the therapy system controller 110 may be configured to receive one or more input signals, such as a feedback signal, and may be configured to modify one or more operating parameters based on the input signals. For example, in some embodiments, the therapy system controller 110 may be configured to receive inputs from one or more other components, for example, from the negative-pressure source 104, from the solution source 114, or from the hyperoxic fluid source 105. Additionally, in the embodiment of FIGS. 1 and 2, the therapy system controller 110 may be configured to receive inputs from a pressure sensor and/or a user interface, as will be disclosed herein. For example, in some embodiments, the therapy system controller 110 may receive input, such as an electrical signal, from a source, such as through an electrical port, for example. In some embodiments, the therapy system controller 110 may be configured to use various inputs to generate an output signal to another component, for example, a signal configured to operate that component. For example, a signal transmitted by the therapy system controller 110 to a particular component, which may be referred to herein as the therapy system controller 110 operating that component, may include signals effective to cause the controlled component to modify any operational parameter associated with that respective component.

In some embodiments, the therapy system controller 110 may include a user interface 118. The user interface 118 may be a device generally configured to allow communication between a controller, such as the therapy system controller 110, and an environment external to controller. In some embodiments, such an external environment may include an operator and, additionally or alternatively, a computer system configured to interface with the system, for example. In some embodiments, the user interface 118 may be configured to receive a signal from the therapy system controller 110 and to present information derived from the signal in a manner that may be received and understood, comprehended, or interpreted by the external environment, such as by a user within the external environment such as a physician, care-giver, or patient. Additionally, in some embodiments, the user interface 118 may be configured to receive input from the external environment and, in response, send signals indicative of the input to the therapy system controller 110.

In some embodiments, the user interface 118 may include a graphical user interface, a touchscreen, and/or one or more motion tracking devices. For instance, the user interface 118 may also include one or more display screens, such as a liquid crystal display ("LCD"), lighting devices, such as light emitting diodes ("LED") of various colors, and audible indicators, such as a whistle, configured to emit a sound that may be heard by an operator. Additionally, in some embodiments the user interface 118 may further include one or more devices, such as knobs, buttons, keyboards, remotes, touchscreens, ports that may be configured to receive a discrete or continuous signal from another device, or other similar devices, which may be configured to permit the external environment to interact with the user interface. For example, the user interface 118 may permit the external environment, for example, a user within the external environment, such as a physician, care-giver, or patient, to select a therapy having a particular characteristic, for example, to be performed by the therapy system 100. In some embodiments, the user interface 118 may display information to the external environment such as a therapy duration, a type of therapy, an amount of reduced pressure being supplied, an amount of hyperoxic fluid being supplied, or an amount of instillation fluid being supplied, for example.

For example, in the embodiment of FIG. 1, the therapy system 100 includes a pressure sensor 116. The pressure sensor 116 is generally configured to detect a pressure and to output a signal indicative of that pressure. For example, the pressure sensor 116 may be in signal communication with the therapy system controller 110. As used herein, the term "signal communication" may refer to a coupling between two or more components that permits the transmission of signals between those components. In various embodiments, the signals may be discrete signals or continuous signals. A discrete signal may be a signal representing a value at a particular instance in a time period. A plurality of discrete signals may be used to represent a changing value over a time period. A continuous signal may be a signal that provides a value for each instance in a time period. The signals may also be analog signals or digital signals. For example, an analog signal may be a continuous signal that includes a time varying feature that represents another time varying quantity. A digital signal may be a signal composed of a sequence of discrete values. Suitable means of providing signal communication between two or more components, as disclosed herein, will be appreciated by one of ordinary skill in the art upon viewing this disclosure. In some embodiments, the signal communication may be one-way communication. In one-way communication, signals may only be sent in one direction. For example, a sensor may generate a signal that may be communicated to a controller, but the controller may not be capable of sending a signal to the sensor. Alternatively, in some embodiments, the signal communication may be two-way communication. In two-way communication, signals may be sent in both directions. For example, a controller and a user interface may be communicatively coupled so that the controller may send and receive signals from the user interface and, likewise, a user interface may send and receive signals from a controller.

Also, the pressure sensor 116 may be in fluid communication with the sealed space 107, for example, such that the pressure sensor 116 may be configured to detect the pressure within the sealed space 107 and to output a signal indicative of the pressure within the sealed space 107. Sensors, such as the pressure sensor 116, are generally known in the art as any apparatus operable to detect or measure a physical phenomenon or property, and generally provide a signal indicative of the phenomenon or property that is detected or measured. The pressure sensor 116 may include any suitable type of so-configured sensor. In some embodiments, the pressure sensor 116 may be a transducer configured to measure pressure in a pneumatic pathway and convert the measurement to a signal indicative of the pressure measured. For example, in various embodiments, the pressure sensor 116 may be a piezoresistive strain gauge, a capacitive sensor, an electromagnetic sensor, a piezoelectric sensor, an optical sensor, or a potentiometric sensor. In some embodiments, a pressure sensor like pressure sensor 116 can measure a strain caused by an applied pressure. Such a pressure sensor may be calibrated by relating a known amount of strain to a known pressure applied. The known relationship may be used to determine an unknown applied pressure based on a measured amount of strain. In some embodiments, a pressure sensor like pressure sensor 116 may include a receptacle configured to receive an applied pressure.

The therapy system controller 110 may also comprise one or more valves, for example, one or more valves configured to control fluid communication via each of the first route of fluid communication 121, the second route of fluid communication 122, and the third route of fluid communication 123, respectively. In such an embodiment, a valve may be generally configured to selectively permit fluid flow therethrough. In various embodiments, such a valve may be configured as a ball valve, a gate valve, a butterfly valve, or other valve type that may be operated to control fluid flow therethrough. Generally, a valve may include a valve body having a flow passage, a valve member disposed in the flow passage and operable to selectively block the flow passage, and an actuator configured to operate the valve member. For example, the actuator may be configured to position the valve member in a closed position, preventing fluid flow through the flow passage of the valve; an open position, permitting fluid flow through the fluid passage of the valve; or a metering position, permitting fluid flow through the flow passage of the valve at a selected flow rate. In an embodiment, the actuator may be an electromechanical actuator configured to be operated in response to the receipt of a signal input. For example, the actuator may include an electrical motor configured to operate upon receipt of a signal from a controller. In response to the signal, the electrical motor of the actuator may move the valve member of the valve. The therapy system controller 110 may be configured to operate the one or more valves so as to cause the therapy system 100 to perform a desired negative pressure and oxygen therapy, as will be disclosed herein. Additionally or alternatively, in some embodiments the therapy system controller 110 may comprise a metering pump, such as a peristaltic pump, to control the application of a fluid to the sealed space 107.

Also, in various embodiments, the therapy system controller 110 includes a power source. The power source may be a device that supplies electrical power to an electric load. In various embodiments, the power source may include a battery, a direct current (DC) power supply, an alternating current (AC) power supply, a linear regulated power supply, a switched-mode power supply, or combinations thereof. For example, in an embodiment, a negative pressure unit may include both an AC power supply and a battery that is charged when AC power is available, for example, via a power converter, and supplies power to one or more components of the negative pressure unit when AC power is unavailable.

While the embodiment of FIG. 1 illustrates the therapy system controller 110, the negative-pressure source 104, the solution source 114, and the hyperoxic fluid source 105 as separate components, in other embodiments, a therapy system controller like the therapy system controller 110 of FIG. 1 may be incorporated within or include the negative-pressure source 104, the hyperoxic fluid source 105, or the solution source 114. Likewise, and additionally, while the embodiment of FIG. 1 illustrates the negative-pressure source 104, the solution source 114, and the hyperoxic fluid source 105 as separate components, in other embodiments, two or more of the negative-pressure source 104, the hyperoxic fluid source 105, and the solution source 114 may integrated, for example, into a commonly housed component.

Figure 2:
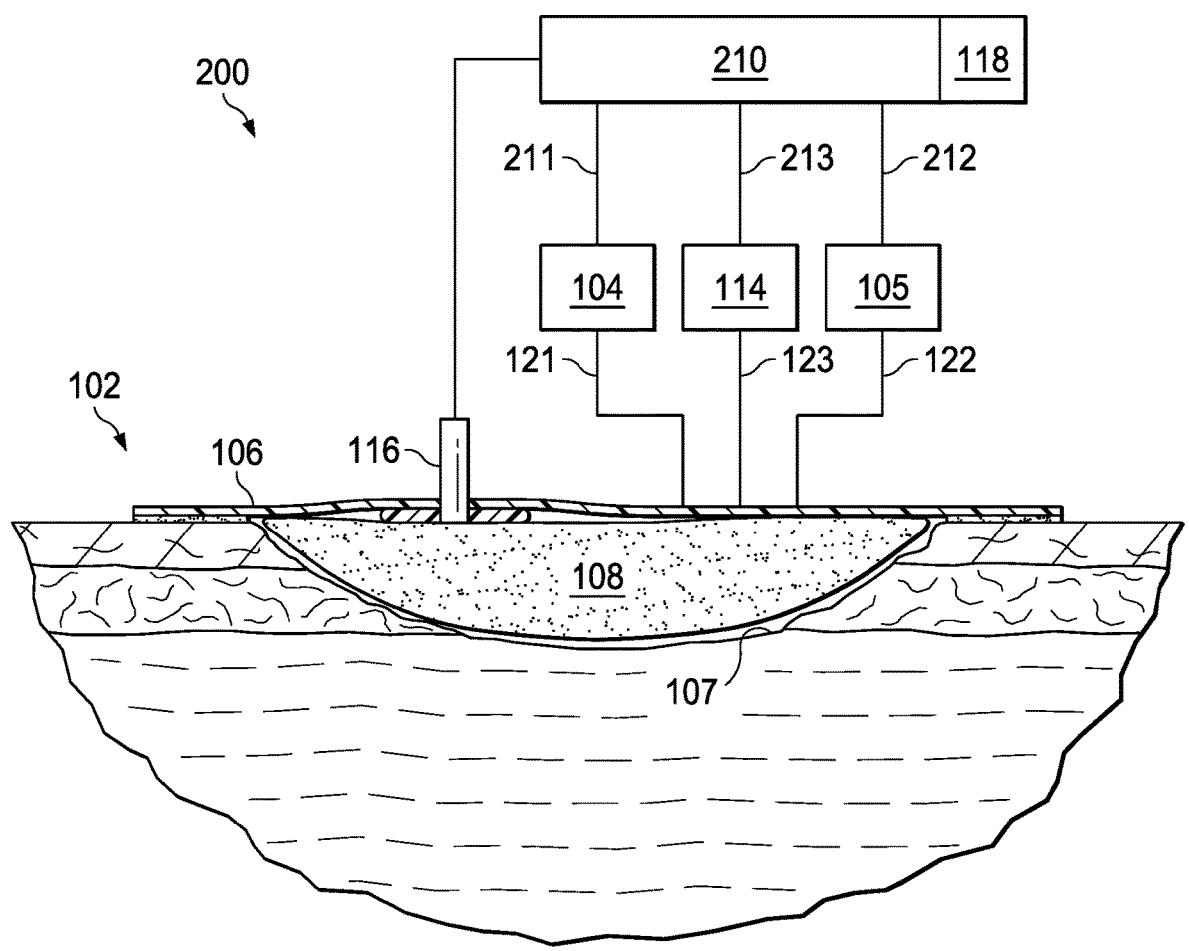
FIG. 2 is a functional schematic of an alternative embodiment of a therapy system for use in negative pressure and oxygen therapy in accordance with this specification.

In other embodiments, the therapy system controller 110 may be configured to control the operation of the negative-pressure source 104, the hyperoxic fluid source 105 and, when included, the solution source 114, for example, such that therapy system 100 is caused to maintain the sealed space 107 at a negative pressure while hyperoxic fluid is provided to the sealed space 107. For example, referring to FIG. 2, a functional schematic of an alternative embodiment of a therapy system 200 is illustrated. In the embodiment of FIG. 2, the therapy system controller 210 may be generally configured to control one or more operational parameters associated with the therapy system or a component thereof, more particularly, one or more operational parameters of the negative-pressure source 104, the hyperoxic fluid source 105, the solution source 114, or combinations thereof. Examples of such operating parameters may include the power applied to the negative-pressure source 104, the negative pressure generated by the negative-pressure source 104, or the negative pressure distributed to the interface layer 108, the power applied to the solution source 114, the solution supplied by the solution source 114 to the interface layer 108, the power applied to the hyperoxic fluid source 105, the hyperoxic fluid generated by the hyperoxic fluid source 105, and the hyperoxic fluid distributed to the interface layer 108.

In the embodiment of FIG. 2, the therapy system controller 210 is in signal communication with the negative-pressure source 104, for example, with a negative-pressure source controller, via a first route of signal communication 211. The therapy system controller 210 is also in signal communication with the solution source 114, for example, with a solution source controller, via a second route of signal communication 212. The therapy system controller 210 is also in signal communication with the hyperoxic fluid source 105, for example, with the hyperoxic fluid source controller, via a third route of signal communication 213.

As also similarly noted with respect to the therapy system controller 110 of FIG. 1, the therapy system controller 210 of FIG. 2 may comprise a microprocessor or other computing device or system (for example, a programmable logic controller or a data processing system). The therapy system controller 210 of FIG. 2 may comprise a user interface generally configured to allow communication between the therapy system controller 210 and an environment external to the therapy system controller 210.

As similarly noted with respect to FIG. 1, while the embodiment of FIG. 2 illustrates the therapy system controller 210, the negative-pressure source 104, the solution source 114, and the hyperoxic fluid source 105 as separate components, in other embodiments, a therapy system controller like the therapy system controller 210 of FIG. 2 may be incorporated within or comprise the negative-pressure source 104, the hyperoxic fluid source 105, or the solution source 114. For example, in various embodiments, one or more of the functionalities disclosed herein with respect to the therapy system controller 210 of FIG. 2 may similarly be performed by the negative-pressure source controller, the solution source controller, or the hyperoxic fluid source controller, or distributed between the negative-pressure source controller, the solution source controller, and/or the hyperoxic fluid source controller. Likewise, and additionally, while FIG. 2 illustrates the negative-pressure source 104, the solution source 114, and the hyperoxic fluid source 105 as separate components, in other embodiments, two or more of the negative-pressure source 104, the solution source 114, and the hyperoxic fluid source 105 source may integrated, for example, into a commonly housed component.

Additionally, in some embodiments, a therapy system controller may be configured both to control one or more of the first route of fluid communication 121, the second route of fluid communication 122, or the third route of fluid communication 123, as disclosed with respect to FIG. 1 and to control the operation of one or more of the negative-pressure source 104, the hyperoxic fluid source 105 and the solution source 114, as disclosed with respect to FIG. 2.

Control Valve

Figure 3A:
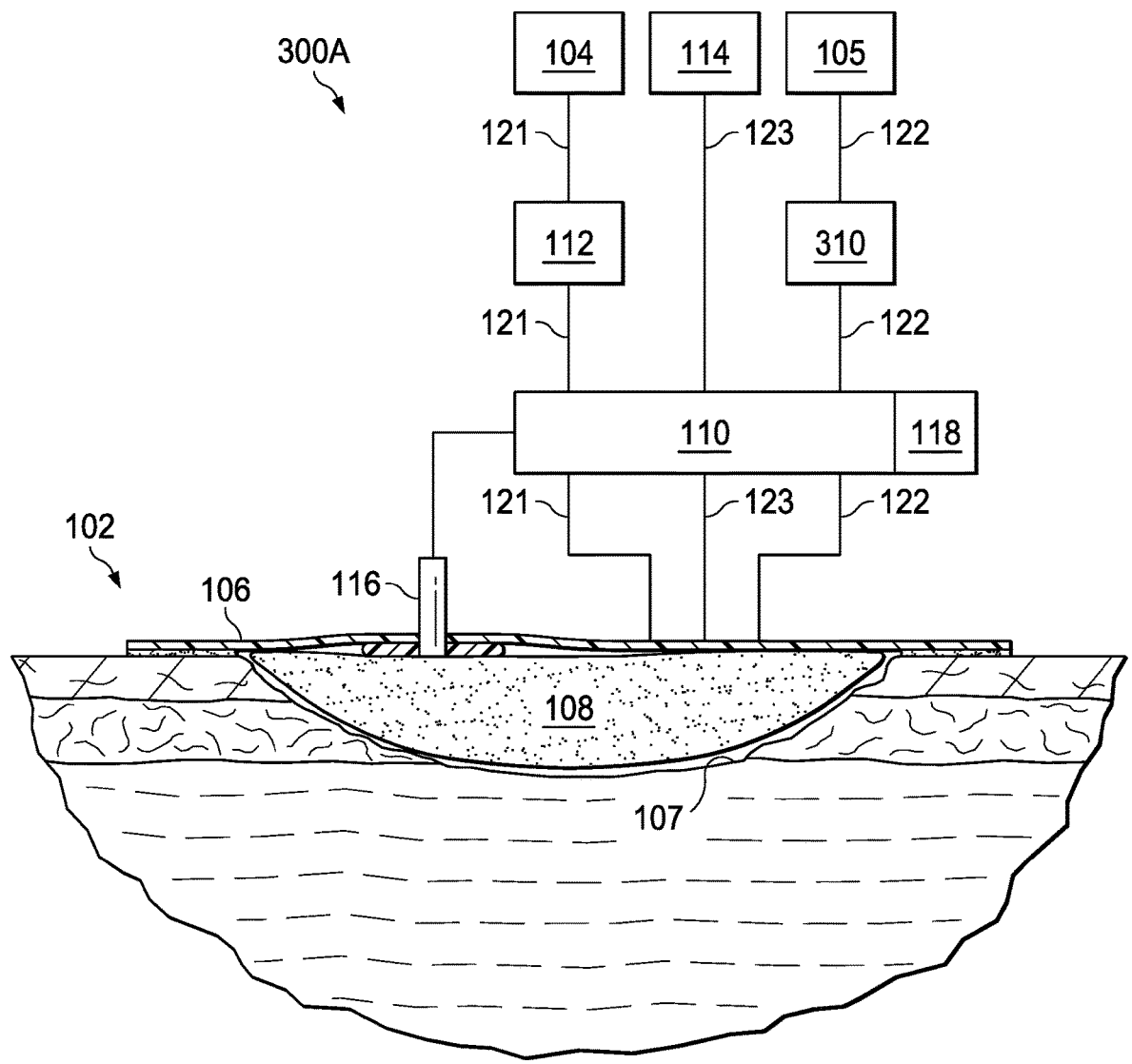
FIG. 3A is a functional schematic of an alternative embodiment of a therapy system for use in negative pressure and oxygen therapy in accordance with this specification.
Figure 3B:
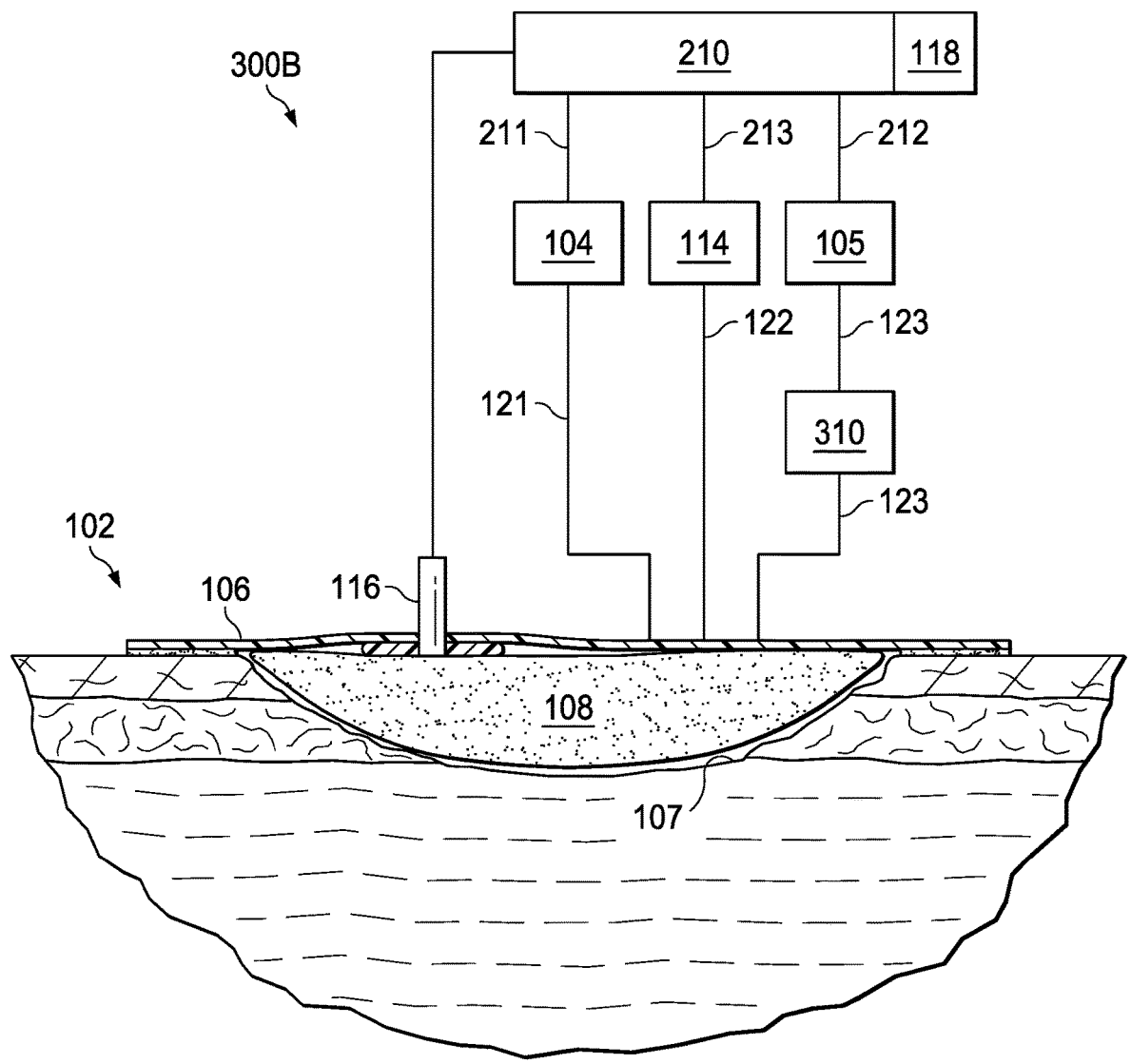
FIG. 3B is a functional schematic of an alternative embodiment of a therapy system for use in negative pressure and oxygen therapy in accordance with this specification.

In some embodiments, a system may further comprise a regulator which may be configured to control the hyperoxic fluid supplied by the hyperoxic fluid source 105. For example, in the embodiment of FIG. 3A, a therapy system 300A, like the therapy system 100 of FIG. 1, comprises a hyperoxic fluid regulator 310. Alternatively, in the embodiment of FIG. 3B, a system 300B like the system of FIG. 2 comprises the hyperoxic fluid regulator 310. In the embodiments of FIGS. 3A and 3B, the hyperoxic fluid regulator 310 may be disposed along a route of fluid communication between the hyperoxic fluid source 105 and the dressing 102, for example, the second route of fluid communication 122. In some, more particular embodiments, the hyperoxic fluid regulator 310 may be located downstream, for example, immediately downstream, from the hyperoxic fluid source 105. In some alternative embodiments, the hyperoxic fluid regulator 310 may be incorporated within the hyperoxic fluid source 105. In some other, alternative embodiments, the hyperoxic fluid regulator 310 may be incorporated within a therapy system controller, for example, within the therapy system controller 110 of FIG. 1.

Figure 4:
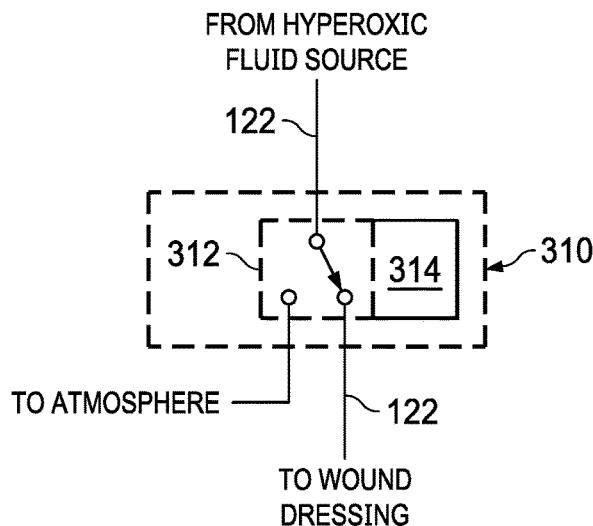
FIG. 4 is a functional schematic of an embodiment of the hyperoxic fluid regulator.

The hyperoxic fluid regulator 310 may be generally configured to regulate the hyperoxic fluid, for example, such that the hyperoxic fluid from the hyperoxic fluid source 105 may be alternated between a first time period and a second time period. During the first time period, the hyperoxic fluid may be drawn into the sealed space 107 via negative pressure within the sealed space 107 and, during the second time period, the hyperoxic fluid is not drawn into the sealed space 107. For example, referring to FIG. 4, an embodiment of the hyperoxic fluid regulator 310 is shown. In the embodiment of FIG. 4, the hyperoxic fluid regulator 310 generally comprises a valve 312 and a valve controller 314. The valve 312 may comprise a three-port valve, for example, a three-way ball valve. Generally, the valve 312 may include a valve body having a first flow passage and a second flow passage, a valve member disposed in the flow passage and operable to selectively provide fluid communication via one of the first or second flow passages, and an actuator configured to operate the valve member. In an embodiment, the actuator may be an electromechanical actuator configured to be operated in response to the receipt of a signal input. For example, the actuator may include an electrical motor configured to operate upon receipt of a signal from the valve controller 314. In the embodiment of FIG. 4, the first flow passage may provide a route of fluid communication to the dressing 102 and the second flow passage provides a route of fluid communication to the atmosphere. In some, alternative embodiments, the second flow passage may provide a route of fluid communication, for example, to a hyperoxic fluid reservoir or to be recycled to the hyperoxic fluid source.

The valve controller 314 may be configured to switch the valve 312 such that fluid communication is provided via the first flow passage for a first time period and the second flow passage for a second time period. In some embodiments, the first time period may be from about 2 to about 10 seconds, more particularly, about 6.5 seconds. Also, in some embodiments, the second time period may be from about 0.5 to about 2 seconds, more particularly, about 1 second.

In operation, the hyperoxic fluid regulator 310 may be effective to deliver bursts of hyperoxic fluid to the dressing 102. In some embodiments the hyperoxic fluid regulator 310 may allow commercially-available hyperoxic fluid source 105 to be employed. For example, a commercially-available example of the hyperoxic fluid source 105, such as the Airsep Focus Portable Oxygen Concentrator, may be designed for use in a breathing treatment, such as in a therapy to treat Chronic obstructive pulmonary disease (COPD). Such devices may be configured to detect a fault or error if those devices do not detect a breathing event. Not intending to be bound by theory, by switching between a route of fluid communication between the hyperoxic fluid source 105 and the dressing 102 and a route of fluid communication between the hyperoxic fluid source and the atmosphere, the hyperoxic fluid regulator 310 may be effective to simulate a breathing event.

Therapy Processes

In various embodiments, a therapy system controller, for example, the therapy system controller 110 of FIG. 1 or the therapy system controller 210 of FIG. 2, may be configured to control the negative pressure from the negative-pressure source, the hyperoxic fluid from the hyperoxic fluid source, and/or the instillation fluid from the solution source so as to provide a therapy. As used in this context, a "therapy" is intended to refer to any suitable combination or sequence of parameters that may be applied to the sealed space 107, for example, a combination of the negative pressure, the hyperoxic fluid, and/or the instillation fluid applied to the sealed space and/or a sequence in which the negative pressure, the hyperoxic fluid, the instillation fluid, or combinations thereof are applied to the sealed space 107. In various embodiments, a therapy may include one or more intervals, for example, a given interval having at least one parameter that differs from the parameters of an adjacent interval. For example, in an embodiment, in a therapy or at least one interval thereof, the sealed space 107 may be maintained at a negative pressure while the hyperoxic fluid is provided to the sealed space 107.

First Therapy Process

Figure 5:
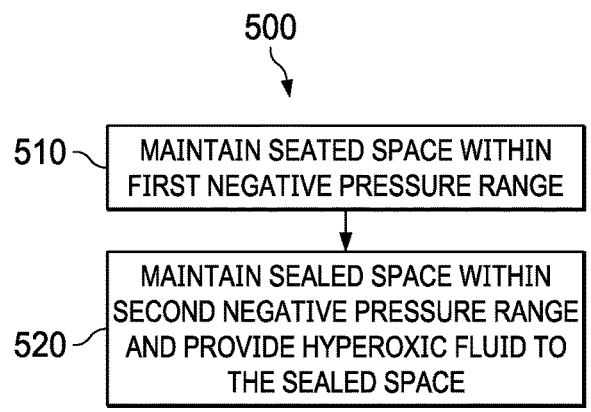
FIG. 5 is an embodiment of a therapy process.

For example, referring to FIG. 5, a first embodiment of a first therapy 500 is illustrated in a diagram. In the embodiment of FIG. 5, the first therapy 500 includes a first interval 510 and a second interval 520.

In various embodiments, during the first interval 510 of the first therapy 500, the sealed space 107 may be maintained within a first negative pressure range. For example, during the first interval 510, a therapy system controller, for example, the therapy system controller 110 of FIG. 1 or the therapy system controller 210 of FIG. 2 may be configured to control the negative pressure, the hyperoxic fluid, and, optionally, the instillation fluid. For example, the therapy system controller 110 may control the respective routes of fluid communication between the sealed space 107 and each of the negative-pressure source 104, the hyperoxic fluid source 105, and the solution source 114, as disclosed with respect to FIG. 1, such that the sealed space 107 is maintained within the first negative-pressure range. Alternatively, the therapy system controller 210 may control the negative-pressure source 104, the hyperoxic fluid source 105, and the solution source 114, as disclosed with respect FIG. 2, such that the sealed space 107 is maintained within the first negative pressure range. The first negative pressure range may be from about −50 mmHg to about −200 mmHg, or more specifically, from about −75 mmHg to about −150 mmHg, or more specifically, from about −100 mmHg to about −125 mmHg. In various embodiments, the first interval may be maintained for a suitable duration, for example, from about 1 hour to about 48 hours.

Also, in various embodiments, during the second interval 520 of the first therapy 500, the sealed space 107 may be maintained within a second negative pressure range while hyperoxic fluid is provided to the sealed space 107. For example, during the second interval 520, the therapy system controller, for example, the therapy system controller 110 of FIG. 1 or the therapy system controller 210 of FIG. 2 may be configured to control the negative pressure, the hyperoxic fluid, and, optionally, the instillation fluid. For example, the therapy system controller 110 may control the respective routes of fluid communication between the sealed space and each of the negative-pressure source 104, the hyperoxic fluid source 105, and the solution source 114, as disclosed with respect to FIG. 1, such that the sealed space 107 is maintained within the second negative pressure range while the hyperoxic fluid is provided to the sealed space 107. Alternatively, the therapy system controller 210 may control the negative-pressure source 104, the hyperoxic fluid source 105, and the solution source 114, as disclosed with respect FIG. 2, such that the sealed space 107 is maintained within the second negative pressure range while the hyperoxic fluid is provided to the sealed space 107. The second negative pressure range may be from about −10 mmHg to about −100 mmHg, or more specifically, from about −20 mmHg to about −75 mmHg, or more specifically, from about −25 mmHg to about −60 mmHg. The pressure within the sealed space 107 during the second interval 520 may be greater than the pressure during the first interval 510. During the second interval 520, the hyperoxic fluid may be provided to the sealed space 107 such that the oxygen concentration within the sealed space rises to at least 80%, more specifically, at least 90%.

For example, in some embodiments, at the conclusion of the first interval 510, the therapy system controller 110 may be configured to allow fluid communication between the sealed space 107 and the hyperoxic fluid source 105, such that hyperoxic fluid is drawn into the sealed space 107 via the negative pressure as maintained during the first interval 510, thereby resulting in an increase in the pressure within the sealed space 107. For example, at the conclusion of the first interval 510, a valve may open to allow hyperoxic fluid to flow into the sealed space 107 until the negative pressure level has decreased to the second negative-pressure range, for example, to be actively communicated from the hyperoxic fluid source 105 to the sealed space 107. Thus, the system may utilize stored potential energy in the form of negative pressure within the sealed space 107 to pull the hyperoxic fluid into the sealed space 107. With the sealed space 107 at the second negative-pressure range, the valve may close to allow increased levels of oxygen to dwell within the sealed spaced 107 while the negative pressure is maintained within the second negative pressure range, for example, such that hyperoxic fluid is not actively communicated from the hyperoxic fluid source 105 to the sealed space 107. Additionally or alternatively, in some embodiments the therapy system controller 110 may be configured to operate a purge valve, for example, to increase the pressure within the sealed space 107. In various embodiments, the second interval may be maintained for a suitable duration.

In various embodiments, a therapy like the first therapy 500 of FIG. 5 may further comprise one or more additional therapy intervals, for example, a third interval, fourth interval, or more, for example, during which negative pressure, a hyperoxic fluid, an instillation fluid, or combinations thereof may be provided to the sealed space 107. In some embodiments, upon completion of the second interval, the therapy may be repeated. For example, the therapy may return to the first interval 510. In various embodiments, the first therapy 500 or a similar therapy may be repeated a particular number of times, for a particular duration, or until a desired result is achieved.

Second Therapy Process

Figure 6:
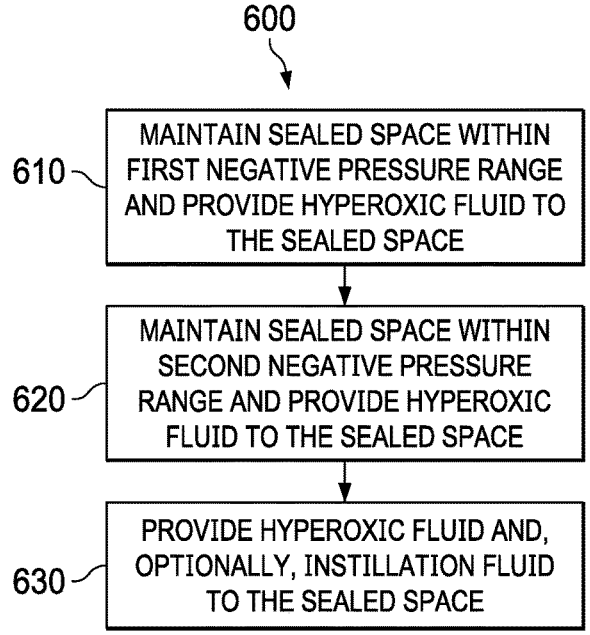
FIG. 6 is an alternative embodiment of a therapy process.

Referring to FIG. 6, a second embodiment of a second therapy 600 is illustrated in a functional diagram. In the embodiment of FIG. 6, the second therapy 600 includes a first interval 610, a second interval 620, and a third interval 630.

In various embodiments, during the first interval 610 of the second therapy 600, the sealed space 107 may be maintained within a first negative pressure range while hyperoxic fluid is provided to the sealed space 107. For example, during the first interval 610, the therapy system controller, for example, the therapy system controller 110 of FIG. 1 or the therapy system controller 210 of FIG. 2 may be configured to control the negative pressure, the hyperoxic fluid, and, optionally, the instillation fluid. For example, the therapy system controller 110 may control the respective routes of fluid communication between the sealed space 107 and each of the negative-pressure source 104, the hyperoxic fluid source 105, and the solution source 114, as disclosed with respect to FIG. 1, such that the sealed space 107 is maintained within the first negative pressure range while hyperoxic fluid is provided to the sealed space 107. Alternatively, the therapy system controller 210 may control the negative-pressure source 104, the hyperoxic fluid source 105, and the solution source 114, as disclosed with respect to FIG. 2, such that the sealed space 107 is maintained within the first negative pressure range while hyperoxic fluid is provided to the sealed space 107. The first negative pressure range may be from about −50 mmHg to about −200 mmHg, or more specifically, from about −75 mmHg to about −150 mmHg, or more specifically, from about −100 mmHg to about −125 mmHg. In various embodiments, the first interval may be maintained for a suitable duration, for example, from about 1 hour to about 48 hours. During the second interval 620, the hyperoxic fluid may be provided to the sealed space 107 such that the oxygen concentration within the sealed space rises to at least 80%, more specifically, at least 90%.

Also, in various embodiments, during the second interval 620 of the second therapy 600, the sealed space 107 may be maintained within a second negative pressure range while hyperoxic fluid is provided to the sealed space 107. For example, during the second interval 620, the therapy system controller, for example, the therapy system controller 110 of FIG. 1 or the therapy system controller 210 of FIG. 2 may be configured to control the negative pressure, the hyperoxic fluid, and, optionally, the instillation fluid. For example, the therapy system controller 110 may control the respective routes of fluid communication between the sealed space and each of the negative-pressure source 104, the hyperoxic fluid source 105, and the solution source 114, as disclosed with respect to FIG. 1, such that the sealed space 107 is maintained within the second negative pressure range while the hyperoxic fluid is provided to the sealed space 107. Alternatively, the therapy system controller 210 may control the negative-pressure source 104, the hyperoxic fluid source 105, and the solution source 114, as disclosed with respect to FIG. 2, such that the sealed space 107 is maintained within the second negative pressure range while the hyperoxic fluid is provided to the sealed space 107. The second negative pressure range may be from about −10 mmHg to about −100 mmHg, or more specifically, from about −20 mmHg to about −75 mmHg, or more specifically, from about −25 mmHg to about −60 mmHg. The pressure within the sealed space during the second interval 620 may be greater than the pressure during the first interval 610. During the second interval, the hyperoxic fluid may be provided to the sealed space 107 such that the oxygen concentration within the sealed space rises to at least 80%, more specifically, at least 90%.

In some embodiments, during the third interval 630 of the second therapy 600, hyperoxic fluid and, optionally, instillation fluid may be provided to the sealed space. The pressure within the sealed space during the third interval 630 may be greater than the pressure during the second interval 620. During the third interval, the hyperoxic fluid may be provided to the sealed space 107 such that the oxygen concentration within the sealed space rises to at least 80%, more specifically, at least 90%.

For example, during the first interval 610, the therapy system controller may be configured to allow fluid communication between the sealed space and the hyperoxic fluid source, for example, such that hyperoxic fluid is drawn into the sealed space 107 via the negative pressure as maintained during the first interval 610. At the conclusion of the first interval 610, the negative pressure within the sealed space 107 may draw hyperoxic fluid into the sealed space 107, while the pressure is allowed to rise within the sealed space 107. Additionally or alternatively, in some embodiments the therapy system controller, for example, the therapy system controller 110 of FIG. 1, may be configured to operate a purge valve, for example, to release negative pressure, for example, to allow an increase of the pressure within the sealed space 107. In various embodiments, the second interval may be maintained for a suitable duration. Also, at the conclusion of the second interval, 620, the negative pressure within the sealed space 107 may draw hyperoxic fluid into the sealed space 107, while the pressure is allowed to rise within the sealed space 107. Additionally or alternatively, in some embodiments the therapy system controller, for example, the therapy system controller 110 of FIG. 1, may be configured to operate a purge valve, for example, to release negative pressure, for example, to allow an increase of the pressure within the sealed space 107.

In various embodiments, a therapy like the second therapy 600 of FIG. 6 may further comprise one or more additional therapy intervals, for example, a fourth interval, a fifth interval, or more, for example, during which negative pressure, a hyperoxic fluid, an instillation fluid, or combinations thereof may be provided to the sealed space 107. In an embodiment, upon completion of the third interval 630, the second therapy 600 may be repeated. For example, the therapy may return to the first interval 610. In various embodiments, the second therapy 600 or a similar therapy may be repeated a particular number of times, for a particular duration, or until a desired result is achieved.

Methods

In operation, the interface layer 108 may be placed within, over, on, or otherwise proximate to a tissue site. The cover 106 may be placed over the interface layer 108 and sealed to an attachment surface near the tissue site. For example, the cover 106 may be sealed to undamaged epidermis peripheral to a tissue site. Thus, the dressing 102 can provide a sealed therapeutic environment proximate to a tissue site, substantially isolated from the external environment. The negative-pressure source 104 may supply negative pressure to reduce the pressure in the sealed space 107; the hyperoxic fluid source 105 may supply hyperoxic fluid to the sealed space 107; and, optionally, the solution source 114 may supply instillation fluids to the sealed space. The negative-pressure source 104, the hyperoxic fluid source 105, and, optionally, the solution source 114 may be operated such that the therapy system is caused to perform a desired therapy, for example, the first therapy 500 disclosed with respect to FIG. 5 or the second therapy 600 disclosed with respect to FIG. 6.

Advantages

In various embodiments, a therapy system like therapy system 100, therapy system 200, therapy system 300A, or therapy system 300A, or components thereof, may be advantageously employed in the provision of negative pressure and oxygen therapy to a patient. For example, and not intending to be bound by theory, by using negative pressure within the sealed space 107 to draw oxygen, for example, the hyperoxic fluid, into the sealed space 107, a healing wound may receive both topical oxygen and negative pressure as a part of the same therapy. For example, as the negative pressure draws oxygen into the sealed space 107, the negative-pressure source 104 may continue to remove air from the sealed space 107 to maintain the pressure within the sealed space 107 within a desired negative-pressure range. As the oxygen, for example, the hyperoxic fluid, is drawn into the sealed space, the oxygen dissipates within the sealed space 107, which can yield an overall increase in the concentration of oxygen within the sealed space 107. As such, as the negative-pressure source 104 and the hyperoxic fluid source 105 are operated to provide negative pressure and oxygen to the sealed space, the fluid removed by the negative-pressure source generally contains less oxygen than is present in the hyperoxic fluid introduced into the sealed space by the hyperoxic fluid source, meaning that the concentration of oxygen within the sealed space 107 generally increases. As such, the disclosed systems and methods may be employed to provide negative pressure and oxygen to a tissue site.

Additionally, using negative pressure within the sealed space 107 to draw oxygen, for example, the hyperoxic fluid, into the sealed space 107 may improve diffusion of the oxygen through the sealed space. For example, in an embodiment where the interface layer 108 is an open-cell, reticulated polyurethane foam such as GRANUFOAM™ dressing, the interface layer 108 to undergo a compression and resultant change in density such that the interface layer 108 exhibits a density of about 0.28 grams/cubic centimeter, at a first negative pressure of about −125 mmHg. Decreasing the negative pressure from about −125 mmHg to about −25 mmHg may cause the interface layer 108 to undergo a decompression and resultant change in density such that the interface layer 108 exhibits a density of about 0.08 grams/cubic centimeter, at a second negative pressure of about −25 mmHg. This decrease in density of the interface layer 108 may facilitate the controlled diffusion of the oxygen molecules throughout the sealed space 107 and, therefore, to the wound.

Figure 7:
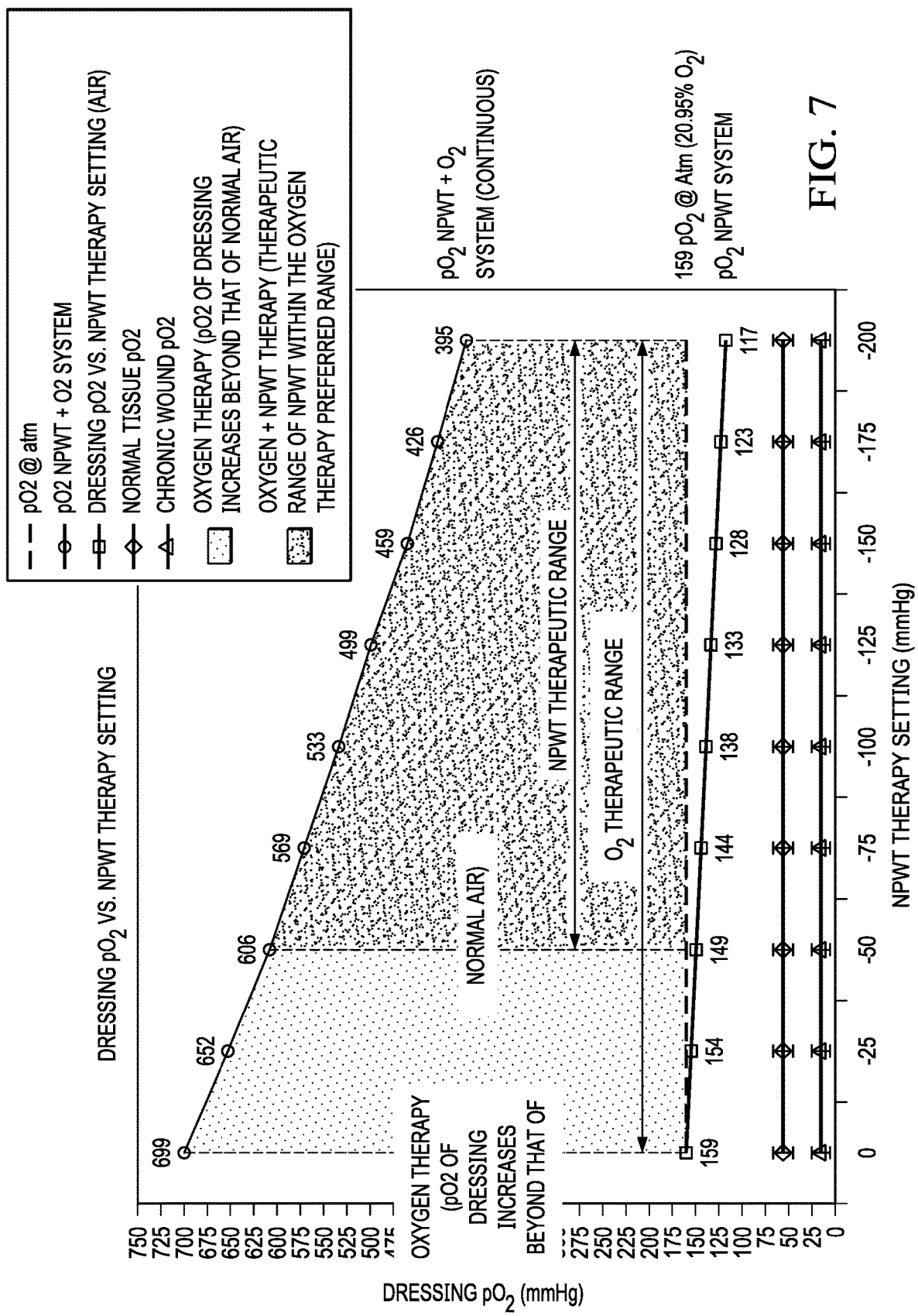
FIG. 7 is a diagram illustrating the relationship between partial oxygen pressure and the negative pressure applied to a tissue site.

Referring to FIG. 7, a diagram illustrating the relationship between partial oxygen pressure and the negative pressure applied to a sealed space, such as the sealed space 107 of FIG. 1, is shown. As shown in FIG. 7, the number of moles of oxygen present within a sealed space is inversely proportional with respect to the negative pressure to the sealed space. More particularly, a sealed space initially having normal, atmospheric air that has been evacuated to −125 mmHg will contain about 0.54 moles/liter of oxygen. Following such a negative pressure cycle at −125 mmHg, 100% oxygen may be infused into the sealed space, for example, thereby allowing the negative pressure within the sealed space to decrease to about −25 mmHg. Based upon Dalton's law of partial pressures and ideal gas mixture theory, the combination of the infusion of oxygen and the decrease in negative pressure level raises the number of moles of oxygen in the sealed space to approximately 0.95 moles/liter, an increase in the moles of oxygen of about 75.2%. Further, by isolating the effect of the decrease in negative pressure from −125 mmHg to −25 mmHg from the effect of the oxygen, the infusion of pure oxygen increases the number of moles of oxygen in the dressing from about 0.63 moles to 0.95 moles/liter, an increase in the moles of oxygen of about 51.3%. Thus, this combination therapy increases the amount of moles of oxygen in the sealed space. While an oxygen source of less than pure oxygen, for example, a hyperoxic fluid having an oxygen content of less than 100%, will exhibit relatively lesser increases in oxygen content as a result of such an oxygen infusion, a hyperoxic fluid as disclosed herein may nonetheless achieve proportionally similar results.

The term "about," as used herein, is intended to refer to deviations in a numerical quantity that may result from various circumstances, for example, through measuring or handling procedures in the real world; through inadvertent error in such procedures; through differences in the manufacture, source, or purity of compositions or reagents; from computational or rounding procedures; and the like. Typically, the term "about" refers to deviations that are greater or lesser than a stated value or range of values by $\frac{1}{10}$ of the stated value(s), for example, ±10%. For instance, a concentration value of "about 30%" refers to a concentration between 27% and 33%. Each value or range of values preceded by the term "about" is also intended to encompass the embodiment of the stated absolute value or range of values. Whether or not modified by the term "about," quantitative values recited in the claims include equivalents to the recited values, for example, deviations from the numerical quantity, but would be recognized as equivalent by a person skilled in the art.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the therapy system controller 110 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for providing treatment to a tissue site, the system comprising:
   a tissue interface configured to transport fluid to and from the tissue site;
   a cover configured to provide a sealed space that includes the tissue interface;
   a negative-pressure source fluidly coupled to the tissue interface and configured to provide negative pressure;
   a hyperoxic fluid source fluidly coupled to the tissue interface and configured to provide a hyperoxic fluid;
   a valve fluidly coupled between the hyperoxic fluid source and the tissue interface; and
   a controller operatively coupled to the negative-pressure source and operatively coupled to the valve, the controller configured to:
      provide a first therapy interval by controlling an operating parameter of the negative-pressure source to maintain the sealed space at a first range of negative pressure,
      send a first signal to open the valve at a conclusion of the first therapy interval to allow negative pressure at the tissue interface to draw the hyperoxic fluid to the tissue interface, and
      send a second signal to close the valve upon negative pressure at the tissue interface reaching a second range of negative pressure.

2. The system of claim 1, wherein the controller is configured to:
   provide a second therapy interval where the sealed space is maintained within the second range of negative pressure by controlling the operating parameter of the negative-pressure source.

3. The system of claim 2, wherein:
   the first range is from about 50 mmHg to about 200 mmHg; and
   the second range is from about −5 mmHg to about −60 mmHg.

4. The system of claim 2, wherein the controller is further configured to:
   send a third signal to open the valve at a conclusion of the second therapy interval to allow negative pressure at the tissue interface to draw the hyperoxic fluid to the tissue interface; and
   send a fourth signal to close the valve upon negative pressure at the tissue interface reaching a third range of negative pressure.

5. The system of claim 2, further comprising:
   a solution source fluidly coupled to the tissue interface; and
   a solution pump configured to provide an instillation solution from the solution source to the sealed space;
   wherein the controller is further configured to provide a third therapy interval comprising:
      maintaining the sealed space within a third range of negative pressure by controlling the operating parameter of the negative-pressure source, and
      operating the solution pump to provide the instillation solution to the sealed space.

6. The system of claim 5, wherein the controller is configured to provide the hyperoxic fluid for the third therapy interval by controlling the operating parameter of the hyperoxic fluid source.

7. The system of claim 5, wherein the third range is from about −5 mmHg to about −60 mmHg.

8. The system of claim 1, wherein the hyperoxic fluid is at least 50 mole percent oxygen gas.

9. The system of claim 1, wherein the tissue interface comprises a polyurethane foam having an uncompressed density in a range of 0.2-0.3 grams per cubic centimeter.

10. A method of providing treatment to a tissue site, the method comprising:
    controlling, using a controller, operating parameters of a negative-pressure source to provide negative pressure to a sealed space around a tissue interface applied to the tissue site;
    maintaining, using the controller, the sealed space within a first range of negative pressure for a first therapy interval by controlling operating parameters of the negative-pressure source;
    sending a first signal from the controller to a valve fluidly coupled between a hyperoxic fluid source and the sealed space to open the valve at a conclusion of the first therapy interval to allow negative pressure at the sealed space to draw the hyperoxic fluid to the sealed space; and
    sending a second signal from the controller to the valve to close the valve upon negative pressure at the sealed space reaching a second range of negative pressure.

11. The method of claim 10, further comprising:
    maintaining, using the controller, the sealed space within the second range of negative pressure for a second therapy interval by controlling operating parameters of the negative-pressure source.

12. The method of claim 11, wherein:
    the first range is from about −100 mmHg to about −150 mmHg; and
    the second range is from about −20 mmHg to about −30 mmHg.

13. The method of claim 11, further comprising:
    sending a third signal from the controller to the valve to open the valve at a conclusion of the second therapy interval to allow negative pressure at the sealed space to draw the hyperoxic fluid to the sealed space; and
    sending a fourth signal from the controller to the valve to close the valve upon negative pressure at the sealed space reaching a third range of negative pressure.

14. The method of claim 11, further comprising:
    controlling, using the controller, operating parameters of the negative-pressure source to maintain the sealed space within a third range of negative pressure for a third therapy interval; and
    providing an instillation fluid to the sealed space for the third therapy interval.

15. The method of claim 14, further comprising providing the hyperoxic fluid for the third therapy interval.

16. The method of claim 14, wherein the third range is from about −5 mmHg to about −60 mmHg.

17. The method of claim 10, wherein the hyperoxic fluid is at least 75 mole percent oxygen gas.

18. The method of claim 14, wherein an oxygen concentration within the sealed space is greater during the second therapy interval than during the first therapy interval, and wherein the oxygen concentration within the sealed space is greater during the third therapy interval than during the first therapy interval or the second therapy interval.

* * * * *

UNITED STATES PATENT AND TRADEMARK OFFICE
CERTIFICATE OF CORRECTION

Page 1 of 1

PATENT NO. : 11,452,809 B2
APPLICATION NO. : 16/495952
DATED : September 27, 2022
INVENTOR(S) : Christopher Brian Locke It is certified that error appears in the above-identified patent and that said Letters Patent is hereby corrected as shown below:

In the Claims

Column 21
Line 43, In Claim 3, delete "50mmHg" and insert -- -50mmHg --, therefor.
Line 43, In Claim 3, delete "200mmHg" and insert -- -200mmHg --, therefor.

Signed and Sealed this
Ninth Day of April, 2024

Katherine Kelly Vidal
*Director of the United States Patent and Trademark Office*